(12) United States Patent
Lux

(10) Patent No.: US 11,771,361 B1
(45) Date of Patent: Oct. 3, 2023

(54) METHOD AND SYSTEM FOR DETERMINING QRS ONSET IN CARDIAC SIGNALS

(71) Applicant: Neucures Inc., Los Angeles, CA (US)

(72) Inventor: Robert L. Lux, Park City, UT (US)

(73) Assignee: NEUTRACE, INC., Longwood, FL (US)

( * ) Notice: Subject to any disclaimer, the term of this patent is extended or adjusted under 35 U.S.C. 154(b) by 31 days.

(21) Appl. No.: 17/073,211

(22) Filed: Oct. 16, 2020

Related U.S. Application Data

(60) Provisional application No. 62/706,024, filed on Jul. 27, 2020.

(51) Int. Cl.
- *A61B 5/00* (2006.01)
- *A61B 5/366* (2021.01)
- *A61B 5/352* (2021.01)

(52) U.S. Cl.
CPC .............. *A61B 5/366* (2021.01); *A61B 5/352* (2021.01)

(58) Field of Classification Search
CPC ............................................. A61B 5/346–366
See application file for complete search history.

(56) References Cited

U.S. PATENT DOCUMENTS

| 2009/0216144 A1* | 8/2009 | Hopenfeld | ........... A61B 5/7239 600/521 |
| 2017/0027463 A1* | 2/2017 | Du | ........................ A61B 5/316 |

* cited by examiner

*Primary Examiner* — Scott M. Getzow
(74) *Attorney, Agent, or Firm* — HM Law Group LLP; Vani Moodley, Esq.

(57) ABSTRACT

A method and system for determining QRS onset in cardiac signals is described. The system and method comprise acquiring N ECG signals and each comprises a plurality of QRS complexes. The system and method further selecting one QRS complex to form the basis of a search for the QRS onset point and defining a starting location within the ECG signal that has the selected QRS complex for the search. Further, the method and system comprises searching backwards in time from said starting location for a first nadir in the signal associated with the selected QRS complex and setting the time of the first nadir as the time for the QRS onset point.

18 Claims, 11 Drawing Sheets

US 11,771,361 B1

METHOD AND SYSTEM FOR DETERMINING QRS ONSET IN CARDIAC SIGNALS

CROSS-REFERENCE TO RELATED PATENT AND PRIORITY

The present application claims priority to US Provisional Patent Application No. 62/706,024 filed on, Jul. 27, 2020, which is hereby incorporated by reference in its entirety.

FILED OF INVENTION

The present disclosure relates to method and system for characterizing signals from the heart. In particular, the present disclosure relates to the determination of QRS onset values from a plurality of cardiac signals.

BACKGROUND

Electrical activity generated by the heart can be measured by an array of electrodes placed on the body surface. The recorded tracing is called an electrocardiogram (ECG, or EKG). The different waves that comprise the ECG represent the sequence of depolarization and repolarization of the atria and ventricles.

Ventricular depolarization is represented by the so-called QRS complex within an ECG. It is desirable in cardiac procedures that the beginning time of ventricular depolarization (i.e. the beginning time of the QRS complex, known hereinafter as "QRS onset") is determined as precisely as possible.

The method described in prior art to determine QRS onset for cardiac signal include first selecting a coarse QRS onset point by comparing the change in the signal over time (i.e. gradient) to a threshold and this coarse onset point is then finetuned by a stepwise decrease of the threshold. Another prior art describes a method for detecting QRS offset by applying a slope test. However, the methods described in the prior art are not effective in determining the exact QRS onset point.

SUMMARY

Before the present method and system for determining QRS onset in cardiac signals, is described, it is to be understood that this application is not limited to the particular system, and methodologies described, as there can be multiple possible embodiments which are not expressly illustrated in the present disclosure. It is also to be understood that the terminology used in the description is for the purpose of describing the particular version or embodiments only and is not intended to limit the scope of the present application. This summary is provided to introduce concepts related to method and system for determining QRS onset in cardiac signals. This summary is not intended to identify essential features of the claimed subject matter nor is it intended for use in determining or limiting the scope of the claimed subject matter.

In an embodiment, a method for determining a QRS onset point for a heartbeat is disclosed. The method comprises acquiring N ECG signal, each comprising a plurality of QRS complexes and selecting one QRS complex to form the basis of a search for the QRS onset point. The method further comprises defining a starting location within the ECG signal that has the selected QRS complex for the search. Further, the method comprises searching backwards in time from said starting location for a first nadir in a specially calculated signal associated with the selected QRS complex and setting the time of the first nadir as the time for the QRS onset point.

In an embodiment, a system for determining a QRS onset point for a heartbeat is disclosed. The system comprises electrical system for recording signal data from a probe when the probe is positioned in a heart of a living subject. The system further comprises a processor and a memory coupled to the processor. The memory is configured to store a set of instructions to be executed by the processor and the processor is configured to acquire N ECG signals, each comprising a plurality of QRS complexes and select, one QRS complex to form the basis of a search for the QRS onset point. The processor is further configured to define, a starting location within the ECG signal that has the selected QRS complex for the search. Further, the processor is configured to search backwards in time from said starting location for a first nadir in the signal associated with the selected QRS complex and set the time of the first nadir as the time for the QRS onset point.

BRIEF DESCRIPTION OF DRAWINGS

The detailed description is described with reference to the accompanying figures. In the figure, the left-most digit (s) of a reference number identifies the figure in which the reference number first appears. The same number are used throughout the drawings to refer like features and components.

DETAILED DESCRIPTION

In the following description, for purposes of explanation, numerous specific details are set forth in order to provide a thorough understanding of the invention.

Reference in this specification to "one embodiment" or "an embodiment" means that a particular feature, structure, or characteristic described in connection with the embodiment is included in at least one embodiment of the invention.

The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not others.

Moreover, although the following description contains many specifics for the purposes of illustration, anyone skilled in the art will appreciate that many variations and/or alterations to said details are within the scope of the present invention. Similarly, although many of the features of the present invention are described in terms of each other, or in conjunction with each other, one skilled in the art will appreciate that many of these features can be provided independently of other features. Accordingly, this description of the invention is set forth without any loss of generality to, and without imposing limitations upon, the invention.

As will be appreciated by one skilled in the art, the aspects of the present invention may be embodied as a system, method or computer program product. Accordingly, aspects of the present invention may take the form of an entirely hardware embodiment, an entirely software embodiment (including firmware, resident software, micro-code, etc.), or an embodiment combining software and hardware aspects that may all generally be referred to herein as a "circuit," "module," or "system." Furthermore, aspects of the present invention may take the form of a computer program product embodied in one or more computer readable medium(s) having computer readable program code embodied thereon.

Figure 1:
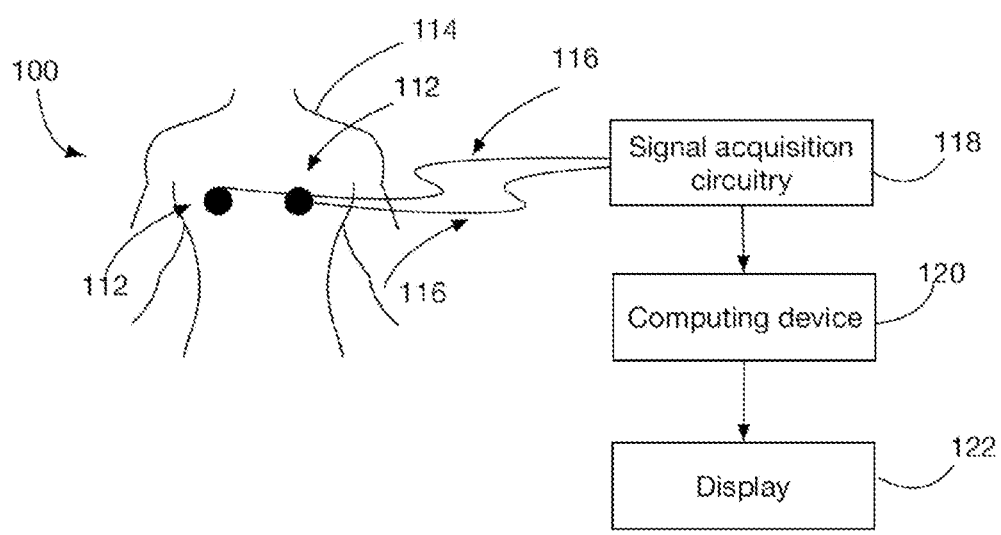
FIG. 1 shows an exemplary system for detecting QRS onset, in accordance with one embodiment of the invention.

FIG. 1 of the drawings shows an exemplary system 100 for acquiring cardiac signals in accordance with one embodiment of the invention. As observed form the figure, the system 100 comprises a plurality of electrodes 112 that may be positioned on the torso of a patient 114. The electrodes 112 may be configured to measure body-surface potentials of the patient 114, e.g. the torso-surface potentials of a patient 114. Each electrode is coupled via an electrical lead 116 to interface/amplifier circuitry 118.

The interface/amplifier circuitry 118 may be configured to amplify the signals from the electrodes 112 and provide the signals to a computing device 120. In other embodiments, a wireless connection may be used to transmit the signals sensed by electrodes 112 to the interface/amplifier circuitry 118 and, in turn, the computing device 120, e.g., as channels of data. For example, the interface/amplifier circuitry 118 may be electrically coupled to each of the computing device 120 using, e.g., analog electrical connections, digital electrical connections, wireless connections, bus-based connections, network-based connections, internet-based connections, etc. The computing device 120 may be operatively coupled to a display device 122 for displaying information to an operator.

The device 120 may record, digitize, and analyse the torso-surface potential signals sensed by electrodes 112 and amplified/conditioned by the interface/amplifier circuitry 118. The computing device 120 may be configured to analyse the signals from the electrodes 112 to provide electrical activation information or data such as cardiac electrical activation (depolarization) times, e.g., representative of actual, or local, electrical activation times of one or more regions of the patient's heart as will be further described herein.

Additionally, the computing device 120 may be configured to provide graphical user interfaces depicting the electrical activation times obtained using the electrodes 112 on the display device 122.

Figure 2:
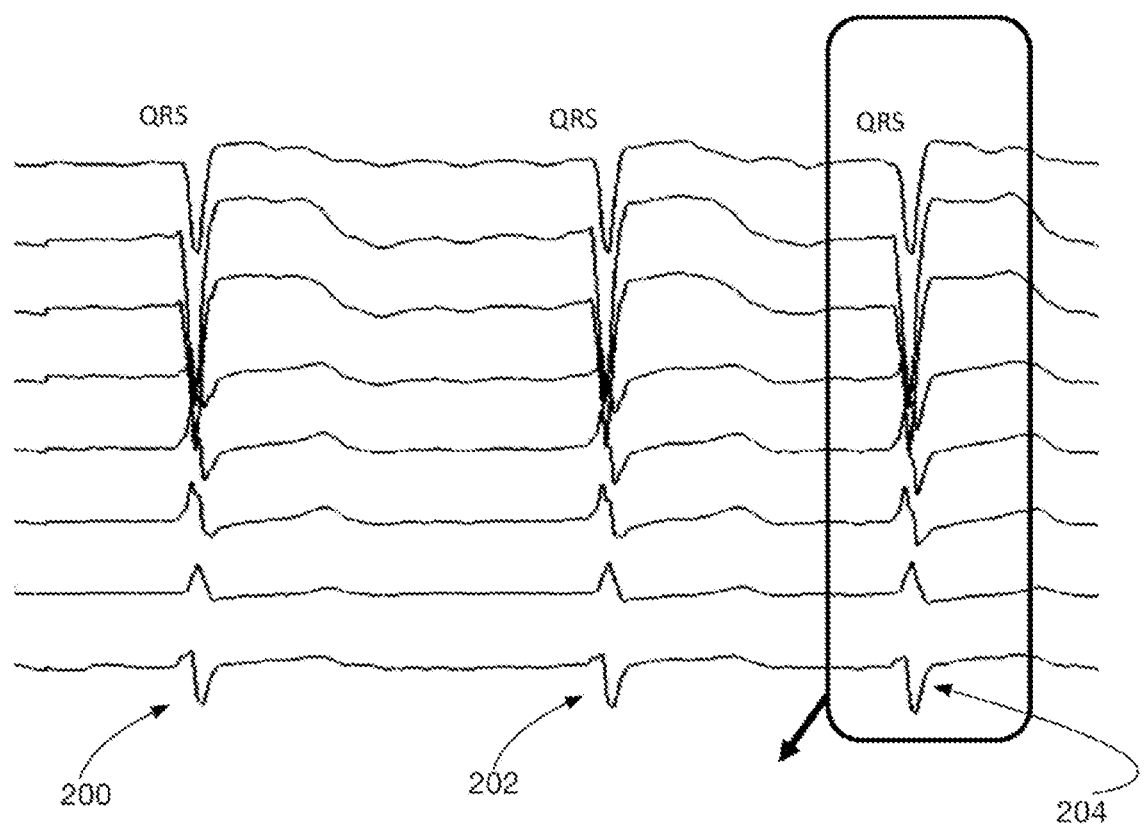
FIG. 2 shows eight body surface ECGs, in accordance with one embodiment of the invention.
Figure 3:
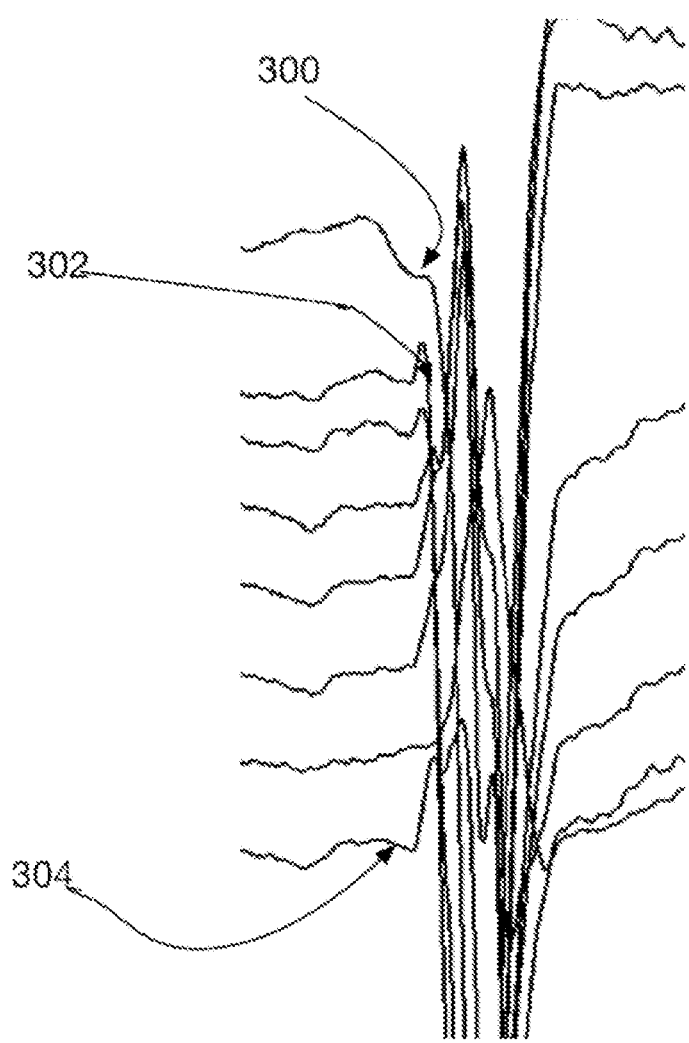
FIG. 3 shows the third beat of the body surface ECGS of FIG. 2 in an expanded scale.

FIG. 2 illustrates eight body ECGs generated by system 100. Each ECG shows three distinct heartbeats represented by reference numerals 200, 202, and 204, respectively. Each ECG represents a voltage signal that indicates a rapid change for each beat that may correspond broadly to the onset of the QRS complex. The recorded signal may not be clean and in most cases may contain noise from the environment. This may cause difficulty in accurately determining the time of the QRS complex with millisecond accuracy. Now consider FIG. 3 that illustrates last beat 204 of FIG. 2 in an expanded form. Arrow 300, 302 and 304 represents points that may be considered as time of QRS onset for the third beat and indicates the difficulty associated with picking the QRS onset point manually.

Figure 4:
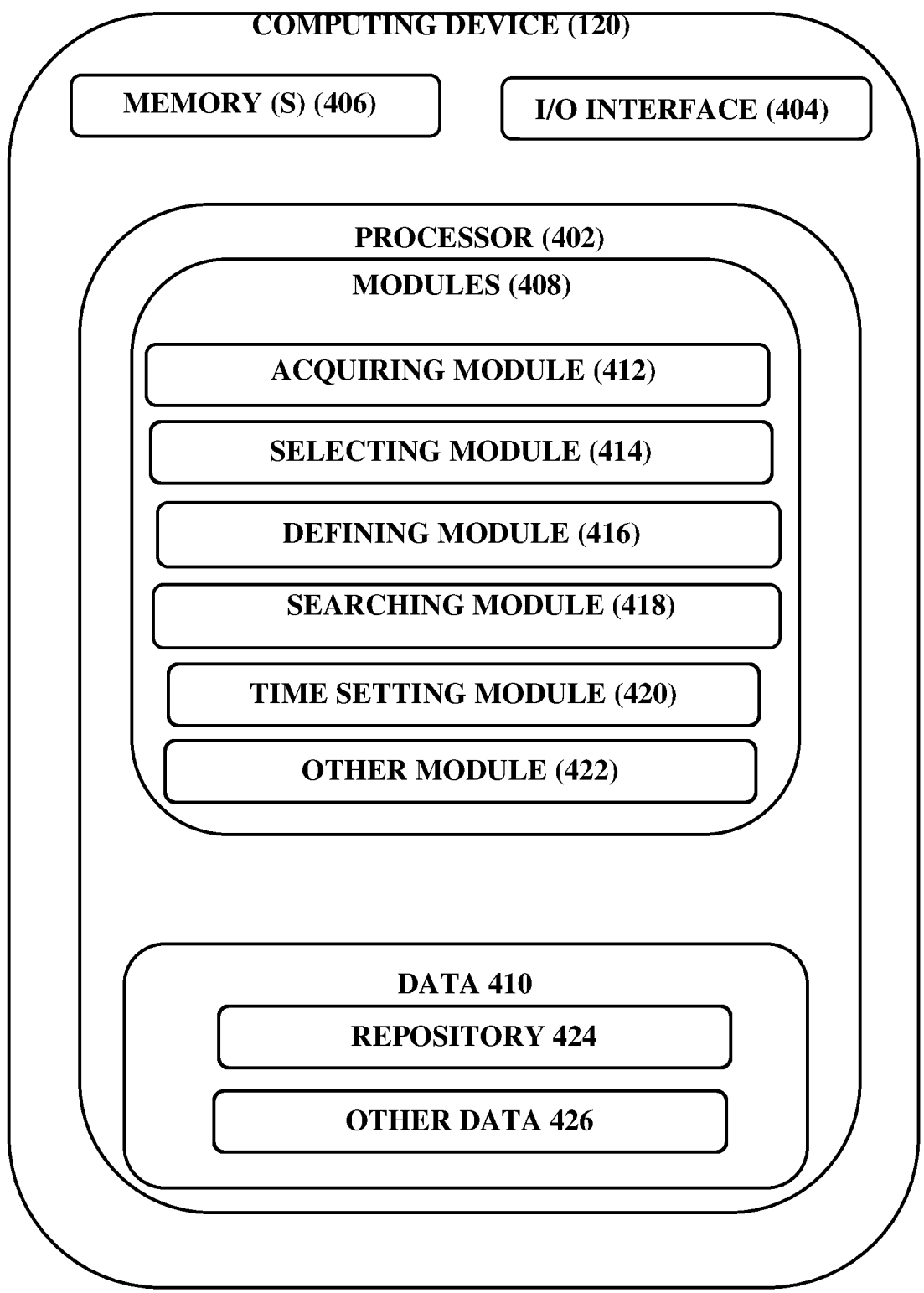
FIG. 4 shows a computing device for detecting QRS onset, in accordance with one embodiment of the invention.

Referring to FIG. 4, a computing device 120 for determining QRS onset in cardiac signals is illustrated in accordance with an embodiment of the present subject matter. In one embodiment, the computing device 120 may include at least one processor 402, an input/output (I/O) interface 404, and a memory 406. The at least one processor 402 may be implemented as one or more microprocessors, microcomputers, microcontrollers, digital signal processors, central processing units, state machine logic circuitries, and/or any device that manipulate signals based on operational instructions. Among other capabilities, at least one processor 402 may be configured to fetch and execute computer-readable instructions stored in the memory 406.

The I/O interface 404 may include a variety of software and hardware interfaces, for example, a web interface, a graphical user interface, and the like. The I/O interface 404 may allow the computing device 120 to interact with the user directly or through the display 122. Further, the I/O interface 404 may enable the computing device 120 to communication with other computing devices, such as web servers and external data servers (not shown). The I/O interface 404 may facilitate multiple communication within a wide variety of networks and protocol types, including wired networks, for example, LAN, cable, etc., and wireless networks, such as WLAN, cellular, or satellite. The I/O interface 404 may include one or more ports for connecting a number of devices to one another or to another server.

In one implementation, a user may access the computing device 120 via the I/O interface. The user may be registered using the I/O interface in order to use the computing device 120. In one aspect, the user may access the I/O interface of the computing device 120 for obtaining information, providing input information or configuring the computing device 120.

The memory 406 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. The memory 406 may include data.

The memory 406 is connected to a plurality of modules 408. The computing module 120 acquiring module 412, selecting module 414, defining module 416, searching module 418, time testing module 420 and other modules 422. The other modules 422 may include programs or coded instructions that supplement applications and functions of the computing device 120.

The data 410, amongst other things, serve as a database for storing data process, received, and generated by one or more of the modules 408. The 410 may also include a repository 424, and other data 426. In one embodiment, the other data 424 may include data generated as a result of the execution of one or more modules in the other modules.

In an embodiment, acquiring module 412 may be configured to acquire N ECG signals continuously and simultaneously and each ECG signals may comprise a plurality of QRS complexes.

In an embodiment, selecting module 414 may be configured to select one QRS complex to form the basis of a search for the QRS onset point. In an embodiment, defining module 416 may be configured to define a starting location with the ECG signal that has the selected QRS complex for the search. The starting location may be selected as the time of a peak in the first derivative with respect to time for the selected QRS complex.

In an embodiment, search module 418 may be configured to search backwards in time from the said starting location for a first nadir in a specially calculated signal associated with the selected QRS complex. The first nadir may be the first nadir below a threshold and the threshold may be defined as a fraction of a peak value associated with the selected QRS complex. The peak value may be defined as a peak in a derivative signal based on the selected QRS complex. The derivative signal corresponds to a signal formed by combining the first and second derivative of the selected QRS complex with respect time and the threshold may be set 0.15 times the peak value. The, search module 418 may be configured to define a window within which the backward search may be constrained, and the window may be set to 300 ms.

In an embodiment, the time setting module 420 may be configured to set the time of the first nadir as the time for the QRS onset point.

Figure 5:
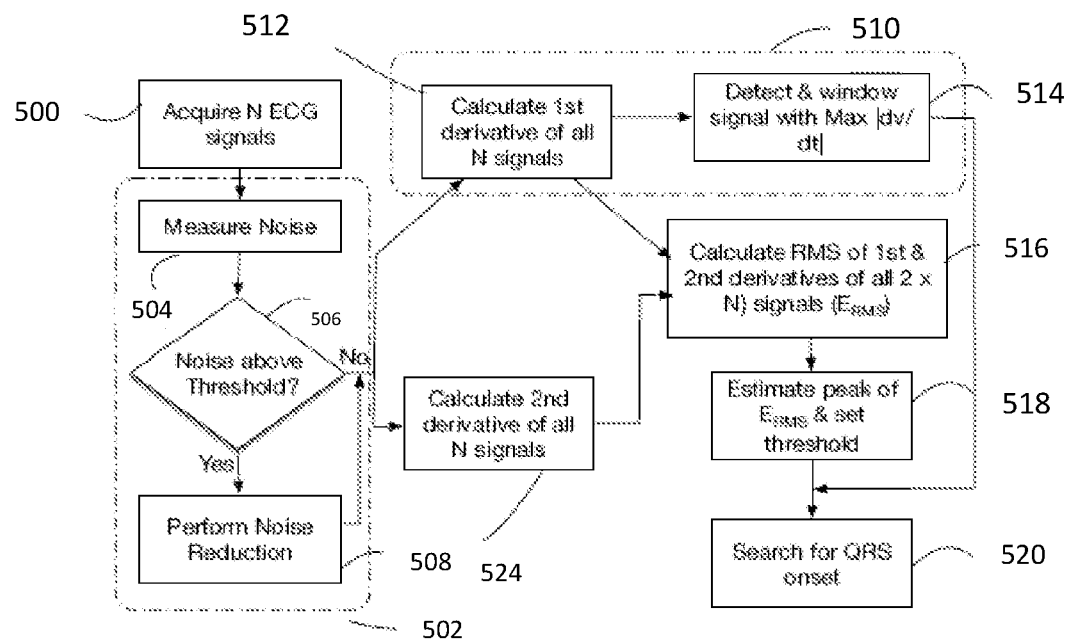
FIG. 5 shows a flowchart for an exemplary method for detecting QRS onset, in accordance with one embodiment of the invention.

FIG. 5 illustrates a flow chart of the operations performed on the ECGS in accordance with the QRS detection method. The N digital ECG signals may be simultaneously and continuously acquired from the unit 118 (block 400). The acquired N digit al ECG signals are indicated generally by reference 600 in that FIG. 6 of the drawings. Processing block 502 is optionally performed to remove noise from the signals. The particular steps included in the processing block 502, in accordance with one embodiment may include measure the noise level in the signals (504), determine if the noise level is above a certain threshold block 506, and if the noise level is above the threshold then perform noise reduction (508). Various techniques may be employed to remove noise detected in the signals. For example, power line or random noise filters may be applied to all ECGs.

Figure 6:
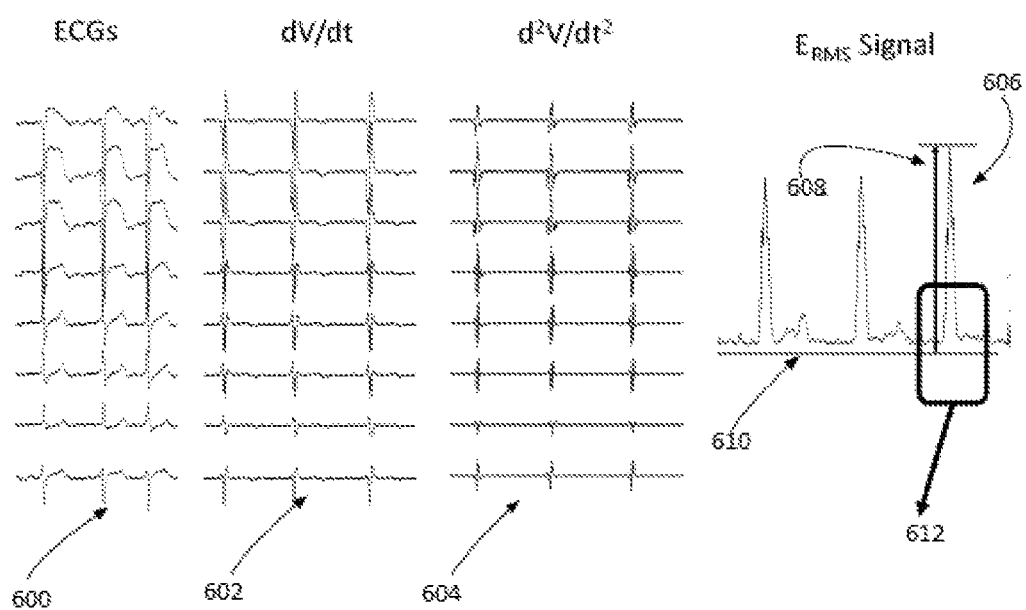
FIG. 6 graphically illustrates some of the operations performed on the ECGs in accordance with the QRS detection method, in accordance with one embodiment of the invention.

Once the N ECG signals with appropriate noise levels are obtained, processing may be transitioned to selection block 510. An output of this block is the selection of one QRS complex/heartbeat for input to a search algorithm to be described. The selection block 510, in accordance with one embodiment of the invention, may include calculating the first derivative of N signals (512). Referring to FIG. 6, reference 602 indicates that the first derivative of the input ECGs 600. The first derivative of the signals may be computed according to the following equation:

Equation for dv/dt:
Least mean squared error (LSME) parabolic fit of data $$j\dot{ECG}_k = A \sum_{i=1}^{n} i(jECG_{k+i} - jECG_{k-i})$$

where jECG is the jth ECG, k is the sample time, and A is dependent on n.

The selection block 510 may also include the step 514 which comprises detecting and windowing the signal that satisfies the condition that the absolute value of dv/dt is at a maximum. In one embodiment the window is a time interval that may be 300 milliseconds prior to that maximum.

Processing block 516 computes the second derivative of all N ECG signals. The output of the processing block 516 is visually indicated by reference 604 in FIG. 6. The second derivative of the signals may be computed according to the following equation:

Equations for $d^2V/dt^2$:
Least mean squared error (LSME) parabolic fit of data $$j\ddot{ECG}_k = B \sum_{i=1}^{n} (jECG_{i+k} + jECG_{i-k}) + C \sum_{i=1}^{n} i^2(jECG_{i+k} + jECG_{i-k})$$

Where B and C are factors dependent on n.

At block 518, the first and second derivatives are combined to form a signal 606 (see FIG. 6). One technique to combine the first and second derivatives may include calculating the mean square ERMS of all 2×N signals.

At block 520, the peak 508 of the ERMS is set for the signal 506 above a baseline 508. The block 520 also establishes the threshold T, which in some embodiments is set to be some fraction of the peak 608, for example 0.15 times the peak value. At block 822, a search is executed for the QRS onset point.

Figure 7:
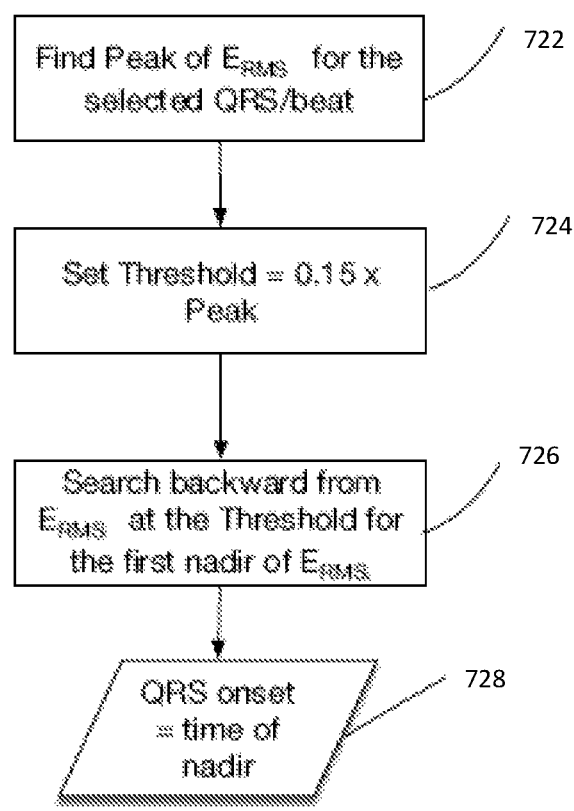
FIG. 7 shows a flowchart for an exemplary method for a search algorithm, in accordance with one embodiment of the invention.

FIG. 7 illustrates the search process to find the time of QRS onset, in accordance with one embodiment. Inputs to the search algorithm include the selected QRS complex/heartbeat based on the techniques disclosed above as well as the calculated ERMS signal. The search algorithm includes block 722 to find the peak 608, and block 724 to find that threshold T. Additionally, the search algorithm includes the block 726 which includes a backward search centred at the peak of the ERMS signal. The search may be conducted within a moving window which may in one embodiment be 300 milliseconds wide. The window is graphically illustrated in FIG. 6 indicated by reference numeral 612. The search is conducted to find the first nadir of the ERMS signal. Thus, the output of the search algorithm at block 726 is the QRS onset which is set to be equal to the time of the first nadir of the ERMS signal.

Figure 8:
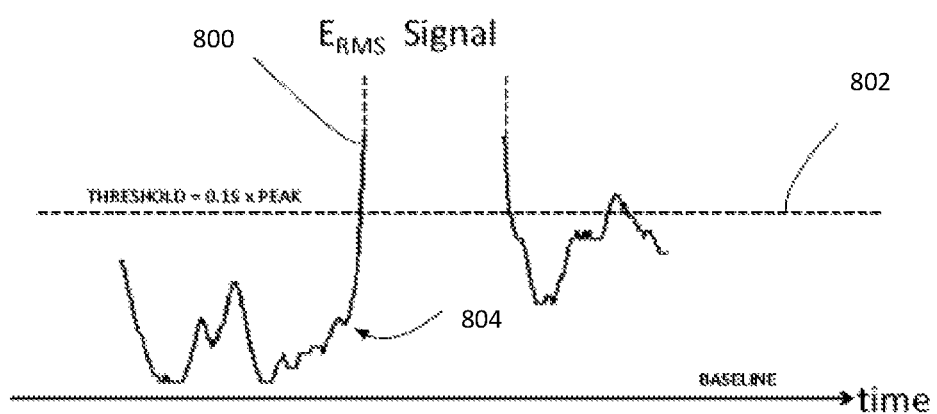
FIG. 8 graphically illustrates some of the operations of the search algorithm, in accordance with one embodiment of the invention.

FIG. 8 graphically illustrates the search process. Referring to FIG. 8 of the ERMS signal 800, with a threshold 802, the search algorithm will pick the first nadir 804 in the signal as the time of the QRS onset.

Figure 9:
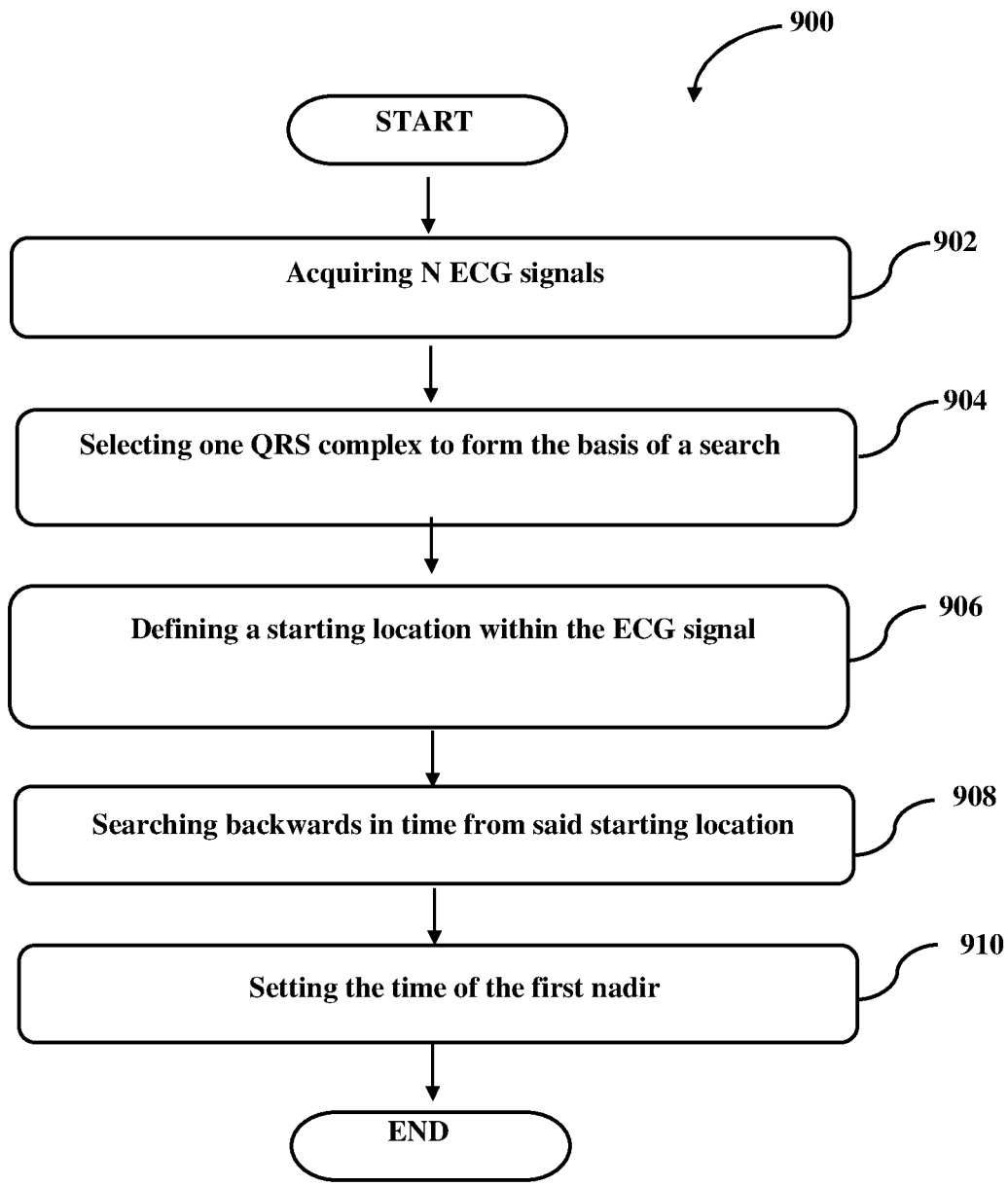
FIG. 9 shows method for detecting QRS onset, in accordance with one embodiment of the invention.

Referring now to FIG. 9, a method 900 for determining QRS onset in cardiac signals, is disclosed in accordance with an embodiment of the present subject matter. The method 900 may be described in the general context of computer executable instructions. Generally, computer executable instructions can include routines, programs, objects, components, data structure, procedures, modules, functions, and the like, that perform particular functions or implement particular abstract data types. The method 900 may also be practiced in a distributed computing environment where functions are performed by remote processing devices that are linked through a communications network. In a distributed computing environment, computer executable instruction may be located in both local and remote computer storage media, including memory storage devices.

The order in which the method 900 is described is not intended to be construed as a limitation, and any number of the described method blocks can be combined in any order to implement the method 900 or alternate methods. Additionally, individual blocks may be deleted from the method 900 without departing from the spirit and scope of the subject matter described herein. Furthermore, the method 900 can be implemented in any suitable hardware, software, firmware, or combination thereof. However, for ease of explanation, in the embodiments described below the method 900 may be considered to be implemented in the above described computing device 120.

At block 902, N ECG signal may be acquired continuously and simultaneously and each ECG signals may comprise a plurality of QRS complexes.

At block 904, one QRS complex may be selected to form the basis of a search for the QRS onset point.

At block 906 the starting location with the ECG signal that has the selected QRS complex for the search may be defined. The starting location may be selected as the time of a peak in the first derivative with respect to time for the selected QRS complex.

At block 908, from the said starting location to determine the first nadir in the ERMS signal associated with the selected QRS complex may be searched backwards in time. The first nadir may be the first nadir below a threshold and the threshold may be defined as a fraction of a peak value associated with the selected QRS complex. The peak value may be defined as a peak in a derivative signal based on the selected QRS complex. The derivative signal corresponds to a signal formed by combining the first and second derivative of the selected QRS complex with respect time and the threshold may be set 0.15 times the peak value. The window may be defined within which the backward search may be constrained, and the window may be set to 300 ms.

At block 910, the time of the first nadir as the time for the QRS onset point may be set.

Figure 10:
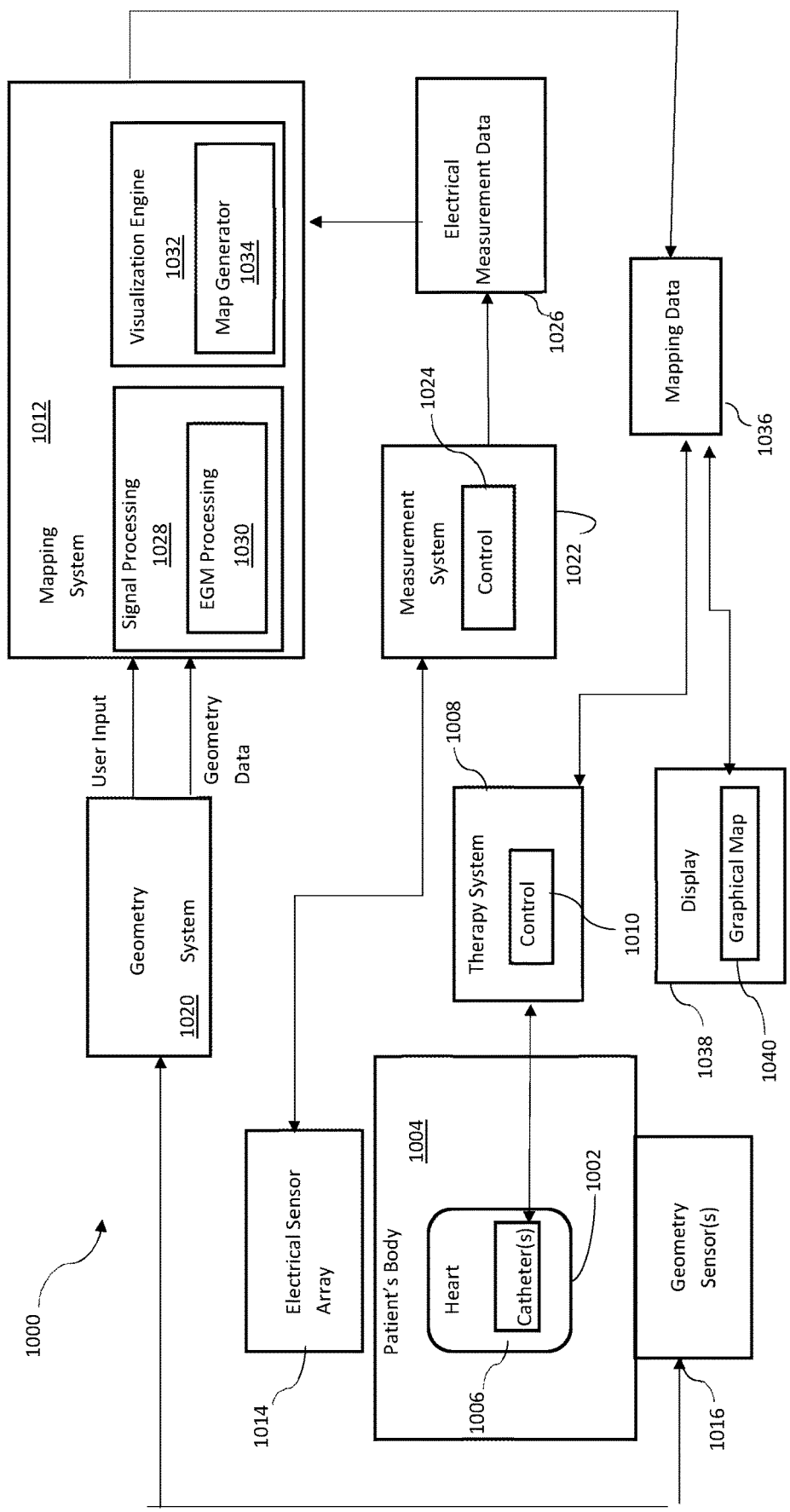
FIG. 10 of the drawings shows an exemplary diagnostic/treatment system, in accordance with one embodiment of the invention.

FIG. 10 of the drawings shows an exemplary diagnostic/treatment system 1000, in accordance with one embodiment of the invention. The system 1000 is capable of assessing the condition of the heart 1002 in real-time as part of a treatment or diagnostic procedure. For this purpose, the system 1000 includes one or more catheters that can be inserted into a patient's body 1004 thereby to contact the patient's heart 1002—more specifically the endocardium or the epicardium. One of ordinary skill in the art would understand and appreciate that various types and configurations of catheters 1006 may be utilized, depending on the type of treatment and procedure.

In some cases, the therapy system 1006 may include one or more electrodes located at the tip of an ablation catheter which in use is configured to ablate tissue in response to electrical signals (for example radiofrequency energy) supplied by a therapy system 1008. In other cases, the therapy delivery device 1006 may include one or more electrodes located at the tip of a pacing catheter to deliver electrical stimulation for pacing the heart in response.

The therapy system 1008 may be located external to the patient's body 1004 and may be configured to control the type of therapy that is delivered by the device 1006. For example, the therapy system 1008 may include control circuitry 1010 configured to deliver electrical signals by a conductive link electrically connected between the device (electrodes) 1006 and the therapy system 1008. The control circuitry 1010 may provide control parameters for the signals supplied to the device 1006 (these may include current, voltage, etc.) For delivering therapy (example ablation) via the electrode(s) 1004 to one or more sites within the heart 1002, the control circuitry 1010 may set therapy parameters and apply stimulation based on automatic, manual (user input) or a combination of automatic and manual mechanisms. In some embodiments, one or more sensors (not shown) may be configured to communicate since the information back to the therapy system 1008. The position of the catheter 1006 within the heart 1002 may be determined and tracked by a mapping system 1002. Location of the device 1006 and in the therapy parameters may be combined to provide corresponding therapy parameters data.

In some embodiments, prior to providing therapy by the therapy system 1008 and other system or subsystem may be utilized to acquire electrophysiological data for the patient. For this purpose, a sensor array 1014 including one or more electrodes may be utilized for recording patient activity. In some cases, the sensor array 1014 may include an arrangement of body surface sensors distributed over a portion of the patient's torso for measuring electrical activity associated with the patient's heart. The catheter 1006 may include one or more electrodes that can be utilized in conjunction with the sensor array 1014 for mapping electrical activity of the endocardial surface such as the wall of the heart chamber. Additionally, such electrodes may be used to obtain location or positional information of the catheter 1006 within the heart which can advantageously be used to register electrical information of the heart in an image or map is generated by the system 1000. In some embodiments, to facilitate the tracking of the catheter 1006 positional within the heart, geometry sensors 1016 may be positioned around the patient's body and configured to sense the position of the catheter 1006 within the heart. For example, in some embodiments, the catheter 1006 may be comprised with a magnetic element that can be sensed by the geometry sensors 1016 to the to derive catheter positional data that is transmitted to a geometry system 1020. The geometry system 1020 may be configured to generate geometry data which is then input into the mapping systems 1012.

In one embodiment, the sensor array 1014 may be configured to provide the sensed electrical information to a corresponding measurement system 1022. The measurement system 1022 may include control circuitry 1024 and signal processing circuitry (not shown) for generating electrical measurement data 1026 that describes electrical activity detected by sensors in the sensor array 1014. The electrical measurement data 1026 may comprise analog and/or digital information. In some embodiments, the control circuitry 1024 may be configured to control a data acquisition process for measuring electrical activity of the heart and generating the electrical measurement data 1026. The electrical measurement data 1026 may be acquired concurrently with the therapy delivered by the therapy system 1008.

The mapping system 1012 may be configured to combine the electrical measurement data 1026 with geometry data generated by the geometry system 1020 by applying appropriate processing computations. For example, the mapping system 1012 may include a single processing module 1028 configured to process the signals generated by the geometry system 1020 and measurements system 1022. For example, the signal processing module 1028 may include an EGM processing module 1030 configured to process EGM signals associated with the heart in accordance with the techniques described above including calculation of the QRS onset. A visualize relation engine 1032 of the mapping systems and 1012 may be provisioned with a mapped generator function 1034 configured to render various metrics associated with the heart in visual form. For this purpose, the visualization engine 1032 outputs mapping data 1036 that can be rendered on a display 1038 as a graphical map 1040 showing various metrics associated with the heart.

By way of example, the geometry data output but the geometry system 1020 may comprise a graphical representation of the patient's torso in the form of image data acquired for the patient. In one embodiment, the geometry system 1020 may process the image data to extract and segment anatomical features of the heart. Additionally, positional information for the sensors within the electrical sensor array 1014 may be included in the geometry data. The geometry data may be converted into a two-dimensional or three-dimensional graphical representation that includes regions of interest within the patient's heart by the mapping systems 1012.

In other embodiments, the geometry data may include a mathematical model of the patient's heart instructed based on image data for the patient. Anatomical or other landmarks, including locations for the electrodes within the sensor array 1014 may be identified in the geometry data to facilitate registration of the electrical measurement data 1026. Identification of said landmarks may be performed manually based on the user input, or automatically by means of image processing techniques.

The mapped generator 1034 may be configured to generate activation maps for the patient's heart, showing various metrics such as electrical activation times, and indications for QRS onset, the DV/DT, fractionation, etc.

In some embodiments, the system 100 acquiring cardiac signals described above may be embedded within the system 1000.

In view of the foregoing structural and functional description, those skilled in the art will appreciate that portions of the invention may be embodied as a method, data processing system, or computer program product. Accordingly, these portions of the present invention may take the form of an entirely hardware embodiment, an entirely software embodiment, or an embodiment combining software and hardware, such as shown and described with respect to the computer system of FIG. 11.

Figure 11:
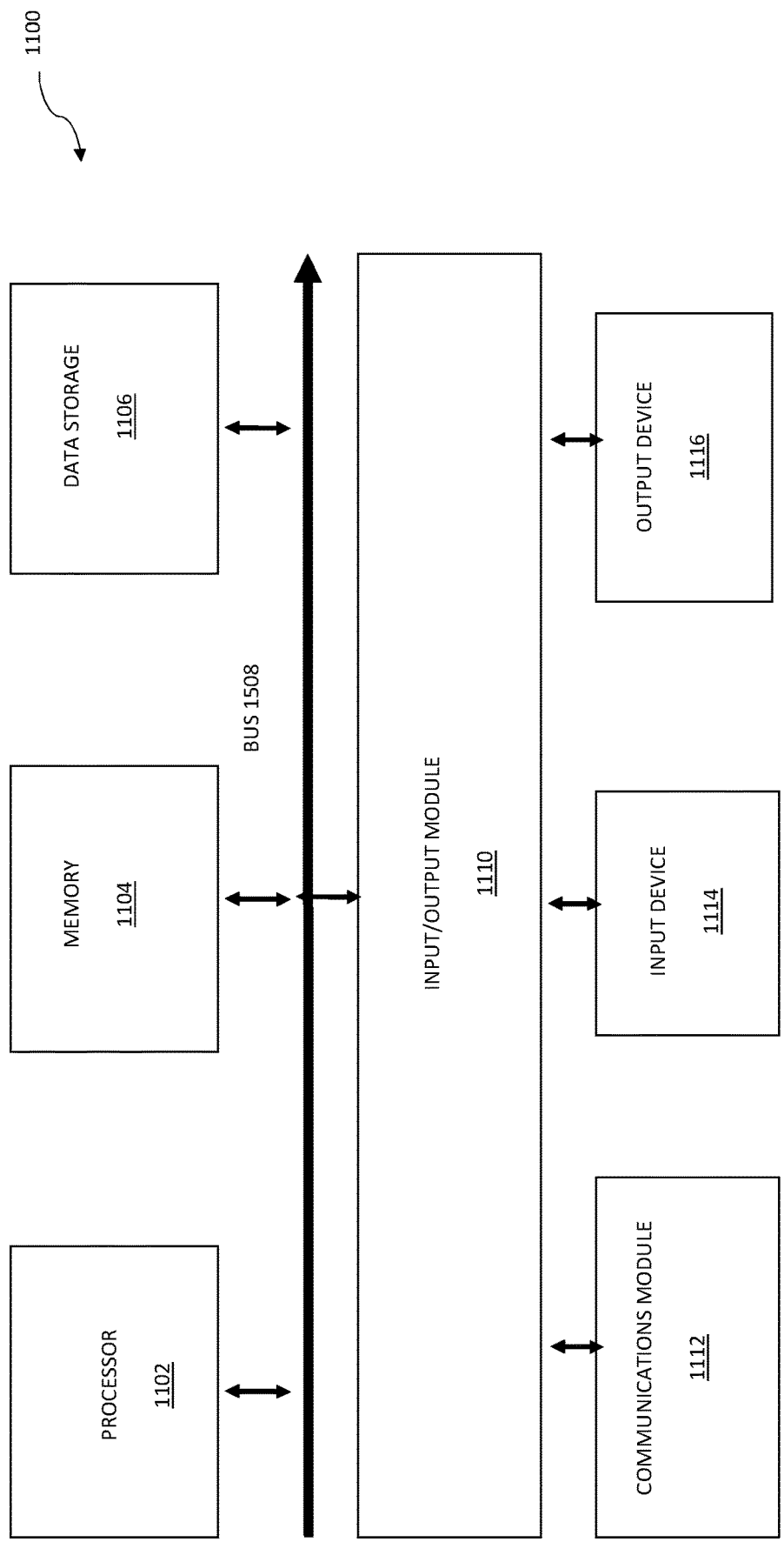
FIG. 11 shows a high-level block diagram of hardware that may be used to practice aspects of the present invention.

FIG. 11 is a block diagram illustrating exemplary hardware for executing some of the techniques disclosed herein, in accordance with one embodiment of the invention. In certain aspects, the computer system 1100 may be implemented using hardware or a combination of software and hardware, either in a dedicated server or integrated into another entity or distributed across multiple entities.

Computer system 1100 (e.g., client or server) includes a bus 1108 or other communication mechanism for communicating information, and a processor 1102 coupled with bus 1108 for processing information. According to one aspect, the computer system 1100 may be implemented as one or more special-purpose computing devices. The special-purpose computing device may be hard-wired to perform the disclosed techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices or any other device that incorporates hard-wired and/or program logic to implement the techniques. By way of example, the computer system 1100 may be implemented with one or more processors 1102. Processor 1102 may be a general-purpose microprocessor, a microcontroller, a Digital Signal Processor (DSP), an ASIC, a FPGA, a Programmable Logic Device (PLD), a controller, a state machine, gated logic, discrete hardware components, or any other suitable entity that can perform calculations or other manipulations of information.

Computer system 1100 can include, in addition to hardware, code that creates an execution environment for the computer program in question, e.g., code that constitutes processor firmware, a protocol stack, a database management system, an operating system, or a combination of one or more of them stored in an included memory 1104 such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, or any other suitable storage device, coupled to bus 1108 for storing information and instructions to be executed by processor 1102. The processor 1102 and the memory 1104 can be supplemented by, or incorporated in, special purpose logic circuitry. Expansion memory may also be provided and connected to computer system 1100 through input/output module 1110, which may include, for example, a SIMM (Single in Line Memory Module) card interface. Such expansion memory may provide extra storage space for computer system 1100 or may also store applications or other information for computer system 1100. Specifically, expansion memory may include instructions to carry out or supplement the processes described above and may include secure information also. Thus, for example, expansion memory may be provided as a security module for computer system 1100 and may be programmed with instructions that permit secure use of computer system 1100. In addition, secure applications may be provided via the SIMM cards, along with additional information, such as placing identifying information on the SIMM card in a non-hackable manner.

The instructions may be stored in the memory 1104 and implemented in one or more computer program products, i.e., one or more modules of computer program instructions encoded on a computer readable medium for execution by, or to control the operation of, the computer system 1100, and according to any method well known to those of skill in the art, including, but not limited to, computer languages such as data-oriented languages (e.g., SQL, dBase), system languages (e.g., C, Objective-C, C++, Assembly), architectural languages (e.g., Java, .NET), and application languages (e.g., PHP, Ruby, Perl, Python). Instructions may also be implemented in computer languages such as array languages, aspect-oriented languages, assembly languages, authoring languages, command line interface languages, compiled languages, concurrent languages, curly-bracket languages, dataflow languages, data-structured languages, declarative languages, esoteric languages, extension languages, fourth-generation languages, functional languages, interactive mode languages, interpreted languages, iterative languages, list-based languages, little languages, logic-based languages, machine languages, macro languages, metaprogramming languages, multiparadigm languages, numerical analysis, non-English-based languages, object-oriented class-based languages, object-oriented prototype-based languages, off-side rule languages, procedural languages, reflective languages, rule-based languages, scripting languages, stack-based languages, synchronous languages, syntax handling languages, visual languages, embeddable languages, and xml-based languages. Memory 1104 may also be used for storing temporary variable or other intermediate information during execution of instructions to be executed by processor 1102.

A computer program as discussed herein does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network. The processes and logic flows described in this specification can be performed by one or more programmable processors executing one or more computer programs to perform functions by operating on input data and generating output.

Computer system 1170 further includes a data storage device 1106 such as a magnetic disk or optical disk, coupled to bus 1108 for storing information and instructions. Computer system 1100 may be coupled via input/output module 1110 to various devices. The input/output module 1110 can be any input/output module. Example input/output modules 1110 include data ports such as USB ports. In addition, input/output module 1110 may be provided in communication with processor 1102, so as to enable near area communication of computer system 1100 with other devices. The input/output module 1110 may provide, for example, for wired communication in some implementations, or for wireless communication in other implementations, and multiple interfaces may also be used. The input/output module 1110 is configured to connect to a communications module 1112. Example communications modules 1112 include networking interface cards, such as Ethernet cards and modems.

The components of the system can be interconnected by any form or medium of digital data communication, e.g., a communication network. The communication network can include, for example, any one or more of a PAN, a LAN, a CAN, a MAN, a WAN, a BBN, the Internet, and the like. Further, the communication network can include, but is not limited to, for example, any one or more of the following network topologies, including a bus network, a star network, a ring network, a mesh network, a star-bus network, tree or hierarchical network, or the like.

For example, in certain aspects, communications module 1112 can provide a two-way data communication coupling to a network link that is connected to a local network. Wireless links and wireless communication may also be implemented. Wireless communication may be provided under various modes or protocols, such as GSM (Global System for Mobile Communications), Short Message Service (SMS), Enhanced Messaging Service (EMS), or Multimedia Messaging Service (MMS) messaging, CDMA (Code Division Multiple Access), Time division multiple access (TDMA), Personal Digital Cellular (PDC), Wideband CDMA, General Packet Radio Service (GPRS), or LTE (Long-Term Evolution), among others. Such communication may occur, for example, through a radio-frequency transceiver. In addition, short-range communication may occur, such as using a BLUETOOTH, WI-FI, or other such transceiver.

In any such implementation, communications module 1112 sends and receives electrical, electromagnetic or optical signals that carry digital data streams representing various types of information. The network link typically provides data communication through one or more networks to other data devices. For example, the network link of the communications module 1112 may provide a connection through local network to a host computer or to data equipment operated by an Internet Service Provider (ISP). The ISP in turn provides data communication services through the world-wide packet data communication network now commonly referred to as the Internet. The local network and Internet both use electrical, electromagnetic or optical signals that carry digital data streams. The signals through the various networks and the signals on the network link and through communications module 1112, which carry the digital data to and from computer system 1100, are example forms of transmission media.

Computer system 1100 can send messages and receive data, including program code, through the network(s), the network link and communications module 1112. In the Internet example, a server might transmit a requested code for an application program through Internet, the ISP, the local network and communications module 1110. The received code may be executed by processor 1102 as it is received, and/or stored in data storage 1106 for later execution.

In certain aspects, the input/output module 1110 is configured to connect to a plurality of devices, such as an input device 1112 (e.g., input device 1114) and/or an output device 1114 (e.g., output device 1114). Example input devices 1112 include a stylus, a finger, a keyboard and a pointing device, e.g., a mouse or a trackball, by which a user can provide input to the computer system 1100. Other kinds of input devices 1112 can be used to provide for interaction with a user as well, such as a tactile input device, visual input device, audio input device, or brain-computer interface device. For example, feedback provided to the user can be any form of sensory feedback, e.g., visual feedback, auditory feedback, or tactile feedback; and input from the user can be received in any form, including acoustic, speech, tactile, or brain wave input. Example output devices 1114 include display devices, such as a LED (light emitting diode), CRT (cathode ray tube), LCD (liquid crystal display) screen, a TFT LCD (Thin-Film-Transistor Liquid Crystal Display) or an OLED (Organic Light Emitting Diode) display, for displaying information to the user. The output device 1114 may comprise appropriate circuitry for driving the output device 1114 to present graphical and other information to a user.

According to one aspect of the present disclosure, the techniques disclosed here in may be implemented on the computer system 1100 in response to processor 1102 executing one or more sequences of one or more instructions contained in memory 1104. Such instructions may be read into memory 1104 from another machine-readable medium, such as data storage device 1106. Execution of the sequences of instructions contained in main memory 1104 causes processor 1102 to perform the process steps described herein. One or more processors in a multi-processing arrangement may also be employed to execute the sequences of instructions contained in memory 1104. in alternative aspects, hard-wired circuitry may be used in place of or in combination with software instructions to implement various aspects of the present disclosure. Thus, aspects of the present disclosure are not limited to any specific combination of hardware circuitry and software.

Various aspects of the subject matter described in this specification can be implemented in a computing system that includes a back end component, e.g., a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components.

Computing system 1100 can include clients and servers. A client and server are generally remote from each other and typically interact through a communication network. The relationship of client and server arises by virtue of computer programs running on the respective computers and having a client-server relationship to each other. Computer system 1100 can be, for example, and without limitation, a desktop computer, laptop computer, or tablet computer. Computer system 1100 can also be embedded in another device, for example, and without limitation, a mobile telephone, a personal digital assistant (PDA), a mobile audio player, a Global Positioning System (GPS) receiver, a video game console, and/or a television set top box.

The term "machine-readable storage medium" or "computer-readable medium" as used herein refers to any medium or media that participates in providing instructions or data to processor 1102 for execution. The term "storage medium" as used herein refers to any non-transitory media that store data and/or instructions that cause a machine to operate in a specific fashion, Such a medium may take many forms, including, but not limited to, non-volatile media, volatile media, and transmission media. Non-volatile media include, for example, optical disks, magnetic disks, or flash memory, such as data storage device 1106. Volatile media include dynamic memory, such as memory 1104. Transmission media include coaxial cables, copper wire, and fiber optics, including the wires that comprise bus 1108. Common forms of machine-readable media include, for example, floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH EPROM, any other memory chip or cartridge, or any other medium from which a computer can read. The machine-readable storage medium can be a machine-readable storage device, a machine-readable storage substrate, a memory device, a composition of matter affecting a machine-readable propagated signal, or a combination of one or more of them.

As used in this specification of this application, the terms "computer-readable storage medium" and "computer-readable media" are entirely restricted to tangible, physical objects that store information in a form that is readable by a computer. These terms exclude any wireless signals, wired download signals, and any other ephemeral signals. Storage media is distinct from but may be used in conjunction with transmission media. Transmission media participates in transferring information between storage media. For example, transmission media includes coaxial cables, copper wire and fiber optics, including the wires that comprise bus 1108. Transmission media can also take the form of acoustic or light waves, such as those generated during radio-wave and infra-red data communications. Furthermore, as used in this specification of this application, the terms "computer", "server", "processor", and "memory" all refer to electronic or other technological devices. These terms exclude people or groups of people. For the purposes of the specification, the terms display or displaying means displaying on an electronic device.

To illustrate the interchangeability of hardware and software, items such as the various illustrative blocks, modules, components, methods, operations, instructions, and algorithms have been described generally in terms of their functionality. Whether such functionality is implemented as hardware, software or a combination of hardware and software depends upon the particular application and design constraints imposed on the overall system. Skilled artisans may implement the described functionality in varying ways for each particular application.

As used herein, the phrase "at least one" of preceding a series of items, with the terms "and" or "or" to separate any of the items, modifies the list as a whole, rather than each member of the list (i.e., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

To the extent that the term "include," "have," or the like is used in the description or the claims, such term is intended to be inclusive in a manner similar to the term "comprise" as "comprise" is interpreted when employed as a transitional word in a claim. Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, sonic configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

A reference to an element in the singular is not intended to mean "one and only one" unless specifically stated, but rather "one or more." The term "some" refers to one or more. Underlined and/or italicized headings and subheadings are used for convenience only, do not limit the subject technology, and are not referred to in connection with the interpretation of the description of the subject technology. Relational terms such as first and second and the like may be used to distinguish one entity or action from another without necessarily requiring or implying any actual such relationship or order between such entities or actions. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description. No claim element is to be construed under the provisions of 35 U.S.C. § 112, sixth paragraph, unless the element is expressly recited using the phrase "means for" or, in the case of a method claim, the element is recited using the phrase "step for."

While this specification contains many specifics, these should not be construed as limitations on the scope of what may be claimed, but rather as descriptions of particular implementations of the subject matter. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

The subject matter of this specification has been described in terms of particular aspects, but other aspects can be implemented and are within the scope of the following claims. For example, while operations are depicted in the drawings in a particular order, this should not be understood as requiring that such operations be performed in the particular order shown or in sequential order, or that all illustrated operations be performed, to achieve desirable results. The actions recited in the claims can be performed in a different order and still achieve desirable results. As one example, the processes depicted in the accompanying figures do not necessarily require the particular order shown, or sequential order, to achieve desirable results. In certain circumstances, multitasking and parallel processing may be advantageous. Moreover, the separation of various system components in the aspects described above should not be understood as requiring such separation in all aspects, and it should be understood that the described program components and systems can generally be integrated together in a single software product or packaged into multiple software products.

The title, background, brief description of the drawings, abstract, and drawings are hereby incorporated into the disclosure and are provided as illustrative examples of the disclosure, not as restrictive descriptions. It is submitted with the understanding that they will not be used to limit the scope or meaning of the claims. In addition, in the detailed description, it can be seen that the description provides illustrative examples and the various features are grouped together in various implementations for the purpose of streamlining the disclosure. The method of disclosure is not to be interpreted as reflecting an intention that the claimed subject matter requires more features than are expressly recited in each claim. Rather, as the claims reflect, inventive subject matter lies in less than all features of a single disclosed configuration or operation. The claims are hereby incorporated into the detailed description, with each claim standing on its own as a separately claimed subject matter.

The claims are not intended to be limited to the aspects described herein but are to be accorded the full scope consistent with the language claims and to encompass all legal equivalents. Notwithstanding, none of the claims are intended to embrace subject matter that fails to satisfy the requirements of the applicable patent law, nor should they he interpreted in such a way.

I claim:

1. A method for determining a QRS onset point for a heartbeat comprising:
    acquiring, N ECG signals, each comprising a plurality of QRS complexes;
    selecting one QRS complex to form the basis of a search for the QRS onset point;
    defining a starting location within the ECG signal that has the selected QRS complex for the search;
    determining a derivative signal of the ECG signal that has the selected QRS complex, wherein the derivative signal is a combination of a first derivative and a second derivative of the selected QRS complex with respect to time;
    searching backwards in time from said starting location for a first nadir in the derivative signal of the ECG signal that has the selected QRS complex; and
    setting the time of the first nadir as the time for the QRS onset point.

2. The method of claim 1, wherein the first nadir is the first nadir below a threshold.

3. The method of claim 2, further comprising defining the threshold as a fraction of a peak value associated with the selected QRS complex.

4. The method of claim 3, wherein said peak value comprises a peak in the derivative signal based on the selected QRS complex.

5. The method of claim 4, wherein the threshold is set at 0.15 times the peak value.

6. The method of claim 1, wherein the starting location is selected as the time of a peak in the first derivative with respect to time for the selected QRS complex.

7. The method of claim 1, wherein selecting the QRS complex comprises:
    calculating the first derivative with respect to time for all ECG signals; and
    selecting that QRS complex wherein an absolute value of said first derivative is at a maximum.

8. The method of claim 1, further comprises defining a window within which to constrain the backwards search.

9. The method of claim 8, wherein said window is set to 300 ms.

10. A system for determining a QRS onset point for a heartbeat comprises:
    electrical system for recording signal data from a probe when the probe is positioned in a heart of a living subject;
    a processor;
    a memory coupled to the processor, wherein the memory is configured to store a set of instructions to be executed by the processor, wherein the processor is configured to:
        acquire, N ECG signals, each comprising a plurality of QRS complexes;
        select one QRS complex to form the basis of a search for the QRS onset point;
        define a starting location within the ECG signal that has the selected QRS complex for the search;
        determine a derivative signal of the ECG signal that has the selected QRS complex, wherein the derivative signal is a combination of a first derivative and a second derivative of the selected QRS complex with respect to time;
        search backwards in time from said starting location for a first nadir in the derivative signal of the ECG signal that has the selected QRS complex; and
        set the time of the first nadir as the time for the QRS onset point.

11. The system of claim 10, wherein the first nadir is the first nadir below a threshold.

12. The system of claim 11, further comprising defining the threshold as a fraction of a peak value associated with the selected QRS complex.

13. The system of claim 12, wherein said peak value comprises a peak in the derivative signal based on the selected QRS complex.

14. The system of claim 13, wherein the threshold is set at 0.15 times the peak value.

15. The system of claim 10, wherein the starting location is selected as the time of a peak in the first derivative with respect to time for the selected QRS complex.

16. The system of claim 10, wherein selecting the QRS complex comprises:
- calculating the first derivative with respect to time for all ECG signals; and
- selecting that QRS complex wherein an absolute value of said first derivative is at a maximum.

17. The system of claim 10, further comprises defining a window within which to constrain the backwards search.

18. The system of claim 17, wherein said window is set to 300 ms.

* * * * *